US012213480B2

(12) United States Patent
Lilly

(10) Patent No.: US 12,213,480 B2
(45) Date of Patent: Feb. 4, 2025

(54) BIOCIDAL FORMULATION

(71) Applicant: For Spills Ltd., Edinburgh (GB)

(72) Inventor: David Lilly, Edinburgh (GB)

( * ) Notice: Subject to any disclaimer, the term of this patent is extended or adjusted under 35 U.S.C. 154(b) by 615 days.

(21) Appl. No.: 17/296,880

(22) PCT Filed: Nov. 27, 2019

(86) PCT No.: PCT/GB2019/053348
§ 371 (c)(1),
(2) Date: May 25, 2021

(87) PCT Pub. No.: WO2020/109786
PCT Pub. Date: Jun. 4, 2020

(65) Prior Publication Data
US 2022/0022450 A1    Jan. 27, 2022

(30) Foreign Application Priority Data

Nov. 28, 2018 (GB) ...................... 1819397

(51) Int. Cl.
| A01N 25/08 | (2006.01) |
| A01N 25/12 | (2006.01) |
| A01N 43/50 | (2006.01) |
| A01N 43/66 | (2006.01) |
| A61L 2/00 | (2006.01) |
| A61L 2/23 | (2006.01) |

(52) U.S. Cl.
CPC ............ *A01N 25/08* (2013.01); *A01N 25/12* (2013.01); *A01N 43/50* (2013.01); *A01N 43/66* (2013.01); *A61L 2/0082* (2013.01); *A61L 2/23* (2013.01)

(58) Field of Classification Search
CPC ..................................................... A01N 25/08
See application file for complete search history.

(56) References Cited

U.S. PATENT DOCUMENTS

| 3,382,170 A | 5/1968 | Hans |
| 3,673,095 A | 6/1972 | Archer |
| 3,985,668 A | 10/1976 | Hartman |
| 4,051,056 A | 9/1977 | Hartman |
| 4,309,247 A | 1/1982 | Hou et al. |
| 4,607,594 A | 8/1986 | Thacker |
| 5,603,896 A | 2/1997 | Rollen |
| 5,638,770 A | 6/1997 | Peleties |
| 5,696,236 A | 12/1997 | Omar et al. |
| 6,083,408 A | 7/2000 | Breitenbach et al. |
| 6,232,521 B1 | 5/2001 | Bewick-Sonntag et al. |
| 6,407,212 B1 | 6/2002 | Morgenthaler et al. |
| 8,226,776 B1 | 7/2012 | Welch et al. |
| 2005/0056229 A1 | 3/2005 | Greene et al. |
| 2007/0065475 A1 | 3/2007 | Elfersy |
| 2008/0139378 A1* | 6/2008 | Hildebrand ........ A01K 1/0152 502/1 |
| 2009/0211981 A1 | 8/2009 | Russo |
| 2009/0232903 A1* | 9/2009 | Sanderson ............ A01N 59/00 424/661 |
| 2014/0230738 A1 | 8/2014 | Goff |
| 2014/0230739 A1 | 8/2014 | Goff |
| 2014/0319059 A1 | 10/2014 | Unhoch |
| 2016/0000291 A1 | 1/2016 | Calderas et al. |
| 2016/0046826 A1 | 2/2016 | Adam et al. |
| 2016/0058008 A1 | 3/2016 | Cao et al. |
| 2017/0267560 A1 | 9/2017 | Coronas Ceresuela et al. |

FOREIGN PATENT DOCUMENTS

| CN | 101703072 A | 5/2010 | |
| CN | 102399653 A | 4/2012 | |
| CN | 105246852 A | 1/2016 | |
| CN | 105925401 A | 9/2016 | |
| DE | 2730266 A1 | 1/1979 | |
| EP | 0281575 A1 | 9/1988 | |
| EP | 1456334 B1 * | 5/2007 | ........... C11D 3/3719 |
| FR | 1479545 A | 5/1967 | |
| FR | 2283653 A1 | 4/1976 | |
| GB | 2043734 A | 10/1980 | |
| GB | 2257053 A | 6/1993 | |
| JP | H04287626 A | 10/1992 | |
| JP | H06343362 A | 12/1994 | |
| JP | H07203793 A | 8/1995 | |
| JP | H0853301 | 2/1996 | |
| JP | H08259413 A | 10/1996 | |
| JP | 2001072519 | 3/2001 | |
| JP | 2011056143 A | 3/2011 | |
| JP | 2014226664 A | 12/2014 | |
| KR | 20130136441 | 12/2013 | |
| KR | 20160024237 A | 3/2016 | |

(Continued)

OTHER PUBLICATIONS

"Freshbin disinfectant powder", Mintel, retrieved from www.gnpd.com.
JPOA, Japanese Office Action dated Sep. 5, 2023 in Application No. 2021-530203.
Chinese Search Report, for Application No. 2019800715630, mailed Feb. 14, 2023.
Chinese Search Report, for Application No. 2019800782372, mailed Dec. 16, 2021.

(Continued)

*Primary Examiner* — Benjamin J Packard
(74) *Attorney, Agent, or Firm* — SNELL & WILMER L.L.P.

(57) ABSTRACT

A dry biocidal absorbent composition comprises an interspersed mixture of a dry absorbent silicate mineral material and a dry biocide. The absorbent silicate mineral material may comprise expanded perlite and/or exfoliated vermiculite. The biocide may comprise sodium dichloroisocyanurate or a hydrate thereof. The composition may be used for cleaning up a bodily spill from a floor or other surface.

17 Claims, No Drawings

(56) References Cited

FOREIGN PATENT DOCUMENTS

| | | | |
|---|---|---|---|
| WO | 9307747 | A1 | 4/1993 |
| WO | 9421775 | A1 | 9/1994 |
| WO | 9501724 | A1 | 1/1995 |
| WO | 9711147 | A1 | 3/1997 |
| WO | 9724092 | A1 | 7/1997 |
| WO | 9858533 | A1 | 12/1998 |
| WO | 2005120221 | A2 | 12/2005 |
| WO | 2006084161 | A2 | 8/2006 |
| WO | 2015047279 | A1 | 4/2015 |
| WO | 2015127528 | A1 | 9/2015 |
| WO | 2017151741 | A1 | 9/2017 |
| WO | 2018048947 | A1 | 3/2018 |

OTHER PUBLICATIONS

EPO; European Search Report dated Jun. 14, 2024 in Application No. 19835469.8.
EPO; European Search Report dated Nov. 26, 2024 in Application 19835469.8.

\* cited by examiner

BIOCIDAL FORMULATION

The present invention relates to cleaning and disinfecting. In particular, the present invention relates to a dry absorbent formulation which has a biocidal effect, and which is particularly useful for cleaning up bodily spills.

The production of bodily spills is an inevitable aspect of life. These often occur in environments such as hospitals, care homes, and agricultural, industrial and domestic spaces, where the hazardous components associated with these spills are unwanted and dangerous. It is apparent then that there is a general need for means to clean up such bodily spills when and where they occur, and to do this in a manner which renders the spills harmless.

The neutralisation or sterilization of bodily spills is one example of a wider field of neutralisation or sterilization which finds use when hazardous substances require to be removed in almost any environment, such as industrial environments, domestic environments, agricultural environments, hospitals, care homes, GP practices, clinics, veterinary practices, workplaces and other institutional environments (offices etc), schools, colleges, catering and entertainment premises, canteens, municipal and other sporting and recreational facilities, swimming pools, retail premises, prisons, police stations and cells.

One known way to deal in the required way with bodily spills, or spills of other hazardous substances, is to use a liquid disinfectant. Any chemical which is to be used to clean up bodily spills needs to be stored. The storage of liquid cleaners can be hazardous in itself and requires additional safety considerations. Furthermore, liquid cleaners do not effectively aid the removal of many spills, especially those spills which are solid or semi-solid.

The present invention is generally directed towards the cleaning and disinfection of spills, for example bodily spills. Bodily spills can take many forms, such as blood, urine, vomit and faeces. They may come from humans; they may come from animals. Whatever their origin, such spills require to be treated in an appropriate manner, as they can pose a risk of transmitting infection or disease. More generally, the application is directed towards the cleaning and disinfection of any spill of hazardous or potentially hazardous nature. A spill can also refer simply to the presence of a hazardous material in a location in which it is not desired or where it poses a hazard.

From a first aspect the present invention provides a dry biocidal absorbent composition comprising an interspersed mixture of a dry absorbent silicate mineral material and a dry biocide.

The silicate mineral material may be expanded. An expanded mineral material can be obtained by heating, which can cause components within the material, for example water, to vaporise. This can result in a lower density, particulate, material, rather than a higher density solid mass.

Alternatively or additionally the silicate mineral material may be exfoliated. Exfoliation is another method of breaking a bulk material down into smaller components, and can result in particles, strands, fibres, flakes or sheet segments. It is commonly used with minerals which contain sheet structures wherein the bonding within each sheet is stronger than the bonding between the sheets.

The absorbent silicate mineral material may be perlite or vermiculite. These materials are, or originate from, naturally occurring minerals. Each of perlite and vermiculite is abundant and of low cost.

One kind of silicate mineral material which we have found to be effective in combination with biocides is expanded perlite. Expanded perlite is prepared from raw perlite by heating to drive off entrapped water thereby resulting in a lower density particulate material.

Another kind of silicate mineral material in accordance with the present invention is exfoliated or expanded vermiculite: this can also be prepared by heat treatment of the corresponding natural mineral material. Typically vermiculite is broken down into smaller fragments by a combination of mechanisms: not only does the layered structure of the vermiculite mineral facilitate exfoliation of layers but also heat treatment drives off entrapped water and breaks the material down further.

The density of the components of the composition can be tailored according to particular requirements. Expanded perlite is a suitable component in many environments including indoor environments. It generally has a lower density than expanded (or exfoliated) vermiculite. Expanded or exfoliated vermiculite can be suitable where heavier components are advantageous, for example outdoor, especially windy, environments. Mixtures of perlite and vermiculite (e.g. mixtures of expanded perlite and exfoliated vermiculite) may be used.

The silicate mineral material may be porous.

Suitably, the composition of the present invention is dry in the sense that water is not present. Furthermore, the composition typically does not comprise any liquid. The composition of the present invention is effective without needing any water or other liquid to be present. The dry silicate mineral and the dry biocide are mixed together and the two components act together in an effective manner so as to absorb material and exert biocidal activity. The mixture is such that the two components may be separate particulate materials, rather than being bonded together, or rather than one component being affixed to or coating the other, or rather than one component being treated with the other. It may be that the composition comprises only these two components.

The dry nature of the composition of the present invention brings several advantages compared to liquid formulations. Some of these advantages relate to handling characteristics. A dry formulation is easy to store. Should a stored dry formulation be upset, then the resulting spill is contained in a way that a liquid would not be. The dry formulation is easy to apply and can be cleared up easily. A dry formulation according to the invention is not overly hazardous when in use, compared to liquid sanitisers which may have a tendency to spread. Such a dry formulation product is easy to dispose of after use. At the same time, this product leads to a significant reduction in bacteria, viruses and/or other harmful organisms present on the floor or other surface after use. The use of dry materials furthermore means that the silicate mineral material is able to exhibit its maximum amount of absorbency because none of its inherent absorbent capacity is reduced by the presence of liquid components which may otherwise adversely affect the ability of the absorbent to absorb external spills.

One area of application for the present invention is the cleaning up of bodily spills. As exemplified below, compositions in accordance with the present invention are particularly effective in absorbing bodily spills and cleaning the area of the spills to result in disinfected surfaces.

Compositions in accordance with the present invention are biocidal. A biocide, typically being a chemical substance, has activity to destroy, deter, render harmless, prevent the action of, or otherwise exert a controlling effect on any harmful organism by chemical or biological means. Biocides are well known and generally subject to regulation.

Biocidal compositions in accordance with the present invention may act as disinfectants in that they can be used on inanimate objects to destroy harmful microorganisms or inhibit their activity. It should be noted that the compositions in accordance with the present invention are not intended to be used on humans or other animals.

Compositions or formulations in accordance with the present invention comprise at least one biocide and may optionally comprise more than one biocide.

Harmful organisms, which may be present in a hazardous biological spill, include:
 harmful viruses, examples being murine parvovirus, poliovirus and adenovirus;
 bacteria, examples of which include *Clostridium difficile*, MRSA, *Staphylococcus aureus, Pseudomonas aeruginosa, Bacillus subtilis* and *Escherichia coif*;
 yeasts and fungi, including *Candida albicans, Aspergillus brasiliensis*, and *Aspergillus niger*.

As will be seen in the examples below, products in accordance with the present invention have effective biocidal activity, kill harmful microorganisms in bodily fluid spills, absorb spills, and leave a floor dry within a few minutes. They are cost effective, efficient and lightweight.

The biocide in accordance with the present invention may optionally be an oxidising biocide. The mode of action of oxidising biocides is such that they have in general a very broad spectrum of efficacy against the majority of unwanted or harmful bacteria, fungi and viruses. Oxidising biocides are in general readily available, and many are of low cost.

Oxidising biocides are a class of biocides known in the art and may for example include biocides the action of which is based on peroxy, or active oxygen, chemistry. These include bleaches. Biocides may include peracids including peracetic acid [which can be generated in situ from the reaction of tetraacetylethylenediamine (TAED) with other components e.g. percarbonates], pentapotassium bis(peroxymonosulphate) bis(sulphate), and magnesium monoperoxyphthalate hexahydrate (MMPP).

Another sub-category of oxidising biocides in accordance with the present invention is that of halogen releasers, for example compounds which can become active in water by releasing free available chlorine or bromine. Free available chlorine can for example be the form of hypochlorous acid (HOCl), which is an effective disinfectant, amongst other species. Similarly, free available bromine can be in the form of hydrobromous acid (HOBr). Halogen releasing biocides include sodium dichloroisocyanurate, or hydrates thereof e.g. the dihydrate, trichloroisocyanuric acid ("symclosene"), 1-bromo-3-chloro-5,5-dimethylhydantoin (often referred to as bromochlorodimethylhydantoin or BCDMH), sodium bromide in combination with for example sodium or calcium hypochorite to release active bromine, and sodium or calcium hypochlorite to release active chlorine. Chloramine releasers, such as chloramine-B and chloramine-T form a further sub-category of oxidising biocides. Sodium chlorite and tetrachlorodecaoxide complex are examples of chemicals which release chlorine dioxide on oxidation. Limes, such as calcium dihydroxide (and related materials calcium hydroxide, caustic lime, hydrated lime, slaked lime), calcium oxide (and related materials lime, burnt lime, quicklime), calcium magnesium oxide (dolomitic lime), and calcium magnesium tetrahydroxide (and related materials calcium magnesium hydroxide and hydrated dolomitic lime) also fall under the category of oxidising biocides.

A characteristic shared by above-mentioned biocides is their capacity to become activated when they change from being in dry form to being in aqueous environments, as will be the case when they come into contact with bodily spills. For example, in the absence of water, compounds such as sodium dichloroisocyanurate or BCDMH, for example, are stable, and, in effect "unactivated", whereas the presence of water results in the generation of active species including hypochlorous acid and hypobromous acid. Similarly the biocidal activity of other compounds, for example chloramine compounds, is triggered in the presence of water.

Halogenated biocides represent an important group of biocides used in the present invention. The combination of these with absorbent silicate mineral materials results in effective formulations which are not only effective absorbents but also quick-acting substances which have a broad spectrum of biocidal activity, in other words they are active against many different microorganisms.

The halogenated biocide may be an alkali metal halocyanurate. Such biocides are in general stable, solid substances which can be readily and conveniently combined with other materials to form a dry formulation.

One possible alkali metal halocyanurate is sodium dichloroisocyanurate. In the dry state, sodium dichloroisocyanurate releases chlorine at an extremely slow rate, thus making it a suitable material to be stored in a container as a part of a dry solid formulation. The rate of chlorine release from solid sodium dichloroisocyanurate is effectively zero under normal storage conditions.

Sodium dichloroisocyanurate releases chlorine (for example in the form of hypochlorous acid) once it is in contact with water, for instance water which is part of a liquid spill.

Other possible oxidising biocides include bromochlorodimethylhydantoin (BCDMH), and a mixture of sodium percarbonate and tetraacetylethylenediamine (TAED) which can be combined to produce peracetic acid, a biocidal active substance.

The prior art discloses the use of some of these types of biocides in various contexts such as the treatment of swimming pool water. In contrast the present invention relates to a conceptually different use and associated composition.

Biocides may also be non-oxidising biocides. Examples of non-oxidising biocides include bronopol and phenolic chemicals, such as orthophenyl phenol (biphenyl-2-ol) and chlorophene (clorophene).

The dry formulation may comprise a mixture of silicate mineral material and biocide wherein the amount of biocide by weight may optionally be 0.1 to 99.9 wt %, (i.e. ranging from a composition in which there is 0.1 parts biocide by weight and 99.9 parts silicate mineral by weight, to a composition in which there is 99.9 parts biocide by weight to 0.1 parts silicate mineral by weight), or 10 to 90 wt %, or 20 to 80 wt %, or 30 to 70 wt %, or 40 to 60 wt %, or 10 to 50 wt %, or 20 to 40 wt %, or 40 to 80 wt %, or 50 to 80 wt %, or 60 to 70 wt %, or at least 1 wt %, or at least 20 wt %, or at least 40 wt %, or at least 50 wt %, or at least 70 wt %, or less than 80 wt %, or less than 60 wt %, or less than 50 wt %, or less than 40 wt %, or less than 30 wt %, or less than 20 wt %.

Optionally, particular particle sizes of silicate mineral material (e.g. perlite) may be used. The particle sizes may be within the range of 300 to 1,700 microns. The average particle size may be in the range of 300 to 1,700 microns. At least 50%, or at least 75%, or at least 90%, or at least 95%, or at least 99%, of the silicate mineral material, by weight, may be composed of silicate mineral material particles falling within the range of 300 to 1,700 microns.

Optionally, instead of 300 to 1,700 microns, the range may be over 300 microns, or 500 to 1,700 microns, or over 500 microns, or 500 to 1,500 microns, or 700 to 1,500 microns, for example.

In broad terms, the absorbent silicate mineral of the formulation serves to absorb liquids and absorb or retain semi-liquids of the bodily spill and thus remove and clean up such liquids and semi-liquids, and the biocide serves as a disinfectant. The present invention allows a disinfecting or sanitising effect which can be greater than that which might be expected from the combination of the individual constituents.

From a further aspect the present invention also provides the use of the formulation as described above in cleaning up and/or disinfecting bodily spills. Use of the formulation in cleaning up bodily spills may utilise the formulation as sole cleaning agent. A quantity of the dry formulation may be applied onto the bodily spill, left for a period of time (referred to as the contact time, for example up to 15 minutes or up to 10 minutes or up to 5 minutes or up to 1 minute), during which the bodily spill is disinfected or sanitised. The resulting residue may then be removed and disposed of in an appropriate manner, e.g. by binning in clinical waste and as would normally be in accordance with regulatory or advisory clinical waste policies of the country, region or site.

Further aspects of the invention are use of the inventive formulation as a bin-sanitiser, as a livestock environment sanitiser, or as a land or ground sanitiser.

As a bin-sanitiser, the formulation can be added to a bin which contains semi-liquid food or animal waste. Once the waste has been absorbed, the residue may be scraped out for disposal.

When used as a sanitiser for areas where livestock are kept or confined, or as a land or ground sanitiser, the formulation may be spread on the floor of an animal stall or pen in order to prevent or inhibit the spread of disease-causing organisms. Subsequent removal of the residue can leave a dry and clean floor.

A quantity of the inventive dry formulation can be contained in a closed container. Said container may be a sachet, for example a sealed sachet, or a sealed bottle. The provision of the dry formulation in such a container has the advantage that the formulation is protected from contamination and humidity. Furthermore, dosed quantities of the different components can be assured when the formulation is required. Problems of settling and segregation of the solid components of the formulation which can occur in large undosed quantities of a mixed material are also avoided. This is an important advantage, given the demonstrated dependence of the sterilizing effect on the relative proportions of the dry ingredients. In other words the use of particular quantities, and particular ratios of silicate mineral material to biocide material, can be assured.

From a further aspect the present invention provides a method of preparing the formulation as described above, comprising mixing the dry biocide with the dry absorbent silicate mineral. The formulation is effective at cleaning bodily spills, and is physically and chemically stable in granular form over lengthy storage times.

Optionally a further material, e.g. a quaternary ammonium compound or mixture of quaternary ammonium compounds, e.g. benzalkonium chlorides, may be incorporated to the dry absorbent silicate mineral prior to the mixing with the dry biocide. Said further material may be applied as a solution, e.g. an aqueous solution, which then dries so that the water or other solvent is removed thereby leaving the further material absorbed into the dry absorbent silicate mineral before the dry biocide is added. The incorporation of the further material may be carried out using a cyclone blender, for example an atomising cyclone blender. For example, a cylinder of such blender may be injected with the further material (e.g. quaternary ammonium compound(s)) which is then absorbed into the mineral particles. Without wishing to be bound by theory it is believed that such blender is advantageous because it facilitates the incorporation of the further material (e.g. quaternary ammonium compounds) into the inside of the particles of the absorbent silicate mineral material (e.g. perlite or vermiculite). The incorporation of such further materials is optional and not an essential feature; in contrast the combination of dry absorbent silicate mineral material and dry biocide is a key characteristic of the present invention.

EXAMPLES

The present invention will now be described in further, non-limiting, detail by summarising some of the experiments which have been carried out.

First Test Series

In a first test, 25 ml of organism (bacterial or mould) suspension was added to 25 ml of 3.0 g/l bovine albumin, simulating a bodily spill. This was left for 2 minutes. The chosen biocide (sodium dichloroisocyanurate; tetraacetylethylenediamine, known as TAED, +sodium percarbonate; or 1-Bromo-3-chloro-5,5-dimethylhydantoin, known as BDCMH) was added to the flask and shaken gently for approximately 5 seconds. The flask was left for the remainder of the 1 minute contact time, before a 1 ml portion of the test mixture was removed and neutralised. This was diluted in neutraliser and all dilutions were plated using the appropriate media in order to measure the remaining concentration of viable bacteria of fungal cells (colony forming units, or cfu).

The results of this test series are presented in the following Table 1. In this table Vc=viable count; N=number of cfu/ml in the bacterial test suspension; Q=quotient of control of weighted mean counts; Nv=number of cfu/ml in the bacterial validation suspension; A=number of cfu/ml in the experimental conditions validation; B=number of cfu/ml in the neutraliser toxicity validation; C=number of cfu/ml in the dilution-neutralisation validation; Na=number of cfu/ml in test mixture after contact time; R=reduction in viability (Log 10). Furthermore, as the upper limit for counting bacterial plates is 330 cfu; counts over this are entered as >330. The upper limit for counting fungal plates is 165 cfu, and counts above this are entered as >165.

TABLE 1

| Test organisms | Bacterial Test Suspension (N) | | Perlite | Sodium Dichloro-isocyanurate | TAED + Percarbonate | BDCMH | Perlite + Sodium Dichloro-isocyanurate | Perlite + TAED + Percarbonate | Perlite + BDCMH |
|---|---|---|---|---|---|---|---|---|---|
| | | | | Controls: Raw test samples | | | Test: Test samples + perlite | | |
| Staphylococcus aureus ATCC 6538 | $10^{-6}$: >330; >330 | N | | | | | | | |
| | $10^{-7}$: 49; 46 | −1 | >330; >330 | 1; 0 | >330; >330 | >330; >330 | 23; 16 | 6; 13 | 1; 6 |
| | | −2 | >330; >330 | 0; 11 | >330; >330 | >330; >330 | 0; 0 | 0; 0 | 0; 0 |
| | | −3 | >330; >330 | 2; 0 | >330; >330 | 284; 251 | 0; 0 | 0; 0 | 0; 1 |
| | | −4 | >330; >330 | 0; 0 | >330; >330 | 38; 48 | 0; 0 | 0; 0 | 0; 0 |
| | | −5 | >330; >330 | 0 0 | 287; 278 | 6; 4 | 0 0 | 0 0 | 0 0 |
| | N: 4.75E+08 | Na | >3.30E+08 | <1.40E+02 | 2.83E+08 | 2.82E+06 | 1.95E+03 | 9.50E+02 | 3.50E+02 |
| | Q: n/a | R | NA | >6.23 | −0.08 | 1.92 | 5.09 | 5.40 | 5.83 |
| Pseudomonas aeruginosa ATCC 15442 | $10^{-6}$: 238; 211 | N | | | | | | | |
| | $10^{-7}$: 34; 23 | −1 | >330; >330 | 236; 160 | >330; >330 | >330; >330 | 128; 216 | 26; 16 | 32; 33 |
| | | −2 | >330; >330 | 60; 34 | >330; >330 | >330; >330 | 0; 2 | 1; 0 | 0; 0 |
| | | −3 | >330; >330 | 33; 35 | >330; >330 | >330; >330 | 0; 0 | 0; 0 | 0; 0 |
| | | −4 | >330; >330 | 10; 14 | >330; >330 | 134; 95 | 0; 1 | 2; 0 | 0; 0 |
| | | −5 | >330; >330 | 2; 9 | 140; 126 | 0; 0 | 0; 0 | 1; 0 | 5; 0 |
| | N: 2.30E+08 | Na | >3.30E+08 | 2.23E+04 | 1.33E+08 | 1.15E+07 | 1.72E+04 | 2.10E+03 | 3.25E+03 |
| | Q: 7.88 | R | NA | 3.71 | −0.06 | 1.00 | 3.83 | 4.74 | 4.55 |
| Aspergillus brasiliensis ATCC 16404 | $10^{-5}$: 157; 171 | N | >165; >165 | >165; >165 | >165; >165 | >165; >165 | 41; 41 | >165; >165 | >165; >165 |
| | $10^{-6}$: 22; 20 | −1 | >165; >165 | 117; 114 | >165; >165 | >165; >165 | 8; 11 | >165; >165 | >165; >165 |
| | | −2 | >165; >165 | 38; 49 | >165; >165 | >165; >165 | 5; 4 | >165; >165 | >165; >165 |
| | | −3 | >165; >165 | 9; 6 | >165; >165 | >165; >165 | 2; 2 | >165; >165 | >165; >165 |
| | | −4 | 102; 102 | 0; 1 | 86; 78 | 92; 98 | 1; 0 | 56; 46 | 52; 70 |
| | | −5 | 14; 16 | 0; 0 | 10; 7 | 19; 20 | 0; 0 | 8; 11 | 10; 8 |
| | N: 2.02E+07 | Na | 1.06E+07 | 1.45E+04 | 8.23E+06 | 1.04E+07 | 4.59E+02 | 5.50E+06 | 6.36E+06 |
| | Q: 7.81 | R | −0.02 | 2.84 | 0.09 | −0.01 | 4.34 | 0.26 | 0.20 |

The above Table 1 presents results of these tests on bacterial strains *Staphylococcus aureus* and *Pseudomonas aeruginosa*, as well as on mould strain *Aspergillus brasiliensis*. The biocidal effect of the biocide is shown in the number Na of colony forming units (cfu) per ml after contact time (see second last row in the table for each test organism), compared to the initial number N of cfu (see column entitled Bacterial Test Suspension (N)). A higher effect results in a lower value of Na. This can also be expressed in a logarithmic scale, represented by R, the reduction in viability (see last row in the table for each test organism). The data in the Table 1 clearly show that the effect of the biocide on bacterial organisms is significantly enhanced through the presence of perlite.

For example, for the two bacterial strains, *Staphylococcus aureus* and *Pseudomonas aeruginosa*, the reduction in viability FIGURES (R expressed in a log scale) given in the table show that TAED+sodium percarbonate alone has effectively no effect (R=−0.08 for *Staphylococcus aureus*; R=−0.06 for *Pseudomonas aeruginosa*). The addition of perlite has a dramatic effect on the effect (R=5.40 for *Staphylococcus aureus*, R=4.74 for *Pseudomonas aeruginosa*). The effect of BDCMH on its own is better (R=1.92 for *Staphylococcus aureus*; R=1.00 for *Pseudomonas aeruginosa*) than TAED+percarbonate, but again improves dramatically with the addition of perlite (R=5.83 for *Staphylococcus aureus*; R=4.55 for *Pseudomonas aeruginosa*).

A clear improvement in the sterilizing effect of sodium dichlorisocyanurate on the mould strain *Aspergillus brasiliensis* is also demonstrated with the addition of perlite (R=2.84 without perlite; R=4.34 with perlite).

Second Test Series

In a second test, the antimicrobial action of a dry formulation was tested. A small amount of a quaternary ammonium compound, specifically in this case benzalkonium chloride (0.36 ml of a 50% solution onto 100 grams of perlite) was added to expanded perlite such that the quaternary ammonium compound was completely absorbed and the perlite was dry. The dry formulation was then prepared by mixing this dry perlite with dry sodium dichloroisocyanurate to produce the dry biocidal formulation. A dry biocidal formulation is produced in this manner with three different proportional compositions: Level 1, comprising 1% (w/w) sodium dichloroisocyanurate to 99% (w/w) treated perlite; Level 2, comprising 10% (w/w) sodium dichloroisocyanurate to 90% (w/w) treated perlite; and Level 3, comprising 20% (w/w) sodium dichloroisocyanurate to 20% (w/w) treated perlite.

The essential components of the formulation are the solid silicate mineral material (here, expanded perlite) and the solid biocide (here, sodium dichloroisocyanurate). The addition to the perlite of a further material, e.g. a quaternary ammonium compound, in a preceding step, is an optional feature; the invention is effective with or without this feature.

The biocidal effect of the above described dry formulations was tested on a variety of surfaces (viz. wood, ceramic, vinyl), each of which was cleaned and disinfected according to standardised procedures prior to testing.

Cultures of a variety of test organisms, as detailed below, were prepared. Each of these cultures was supplied to a surface by pipetting a 5 ml mixture of the organism and a suspension of a mixture of bovine albumin (3.0 g/l) and sheep erythrocytes (3.0 ml/L). The mixture of bovine albumin (3.0 g/l) and sheep erythrocytes simulates a bodily spill. For tests involving viruses, a medium/serum solution was also included in the mixture. In this manner the test surfaces were prepared. Tests were performed for three different contact times (1 min, 5 mins and 10 mins). For each of these contact times, each test surface was prepared in duplicate.

Tests were performed for each of the following organisms prepared in culture:
  *Staphylococcus aureus* (bacterial strain)
  *Pseudomonas aeruginosa* (bacterial strain)
  *Candida albicans* (yeast strain)
  *Aspergillus brasiliensis* (conidiospores)

*Bacillus subtilis* ATCC 6633 (bacterial spore strain)
Adenovirus 5
Poliovirus 1
Murine parvovirus To test the sterilizing effect of the dry perlite formulation, a pre-weighed amount of the perlite formulation was added to each test surface and then left there for the contact time. At the end of the contact time, the surface was scraped to remove the residue. Organisms still surviving on the surface were then recovered using diluent and swabbing. A standard assay procedure was then used to determine the concentration of surviving organisms.

Second Test Series Results

A logarithmic scale is used in the presentation of the results. For example, when a disinfection reduces $10^8$ bacteria to $10^2$ bacteria, this is a logarithmic reduction of 6; when a disinfection reduces $5 \times 10^7$ fungal spores to $8 \times 10^3$ fungal spores this is a logarithmic reduction of 3.79.

The results of the second test series are shown in the following tables. Each table represents surface test results for strains at three concentrations (Level 1=1.0% W/W sodium dichloroisocyanurate; Level 2=10.0% W/W sodium dichloroisocyanurate; Level 3=20.0% W/W sodium dichloroisocyanurate) for 1 minute, 5 minutes and 10 minutes contact time at 20° C. on three representative surfaces. Results are expressed by the mean log reduction and standard deviation (s.d.) (N=2).

The first two sets of test results in this series relate to antibacterial activity.

*Staphylococcus aureus*, Perlite+Sodium Dichloroisocyanurate

TABLE 2

| Level | Contact time | Wood Mean | wood s.d | ceramic mean | ceramic s.d | vinyl mean | vinyl s.d |
|---|---|---|---|---|---|---|---|
| Level 1 | 1 min | 2.40 | 0.08 | 2.53 | 0.24 | 2.61 | 0.35 |
| | 5 min | 2.21 | 0.08 | 2.42 | 0.02 | 2.46 | 0.06 |
| | 10 min | 2.65 | 0.70 | 2.42 | 0.37 | 3.29 | 1.00 |
| Level 2 | 1 min | 2.11 | 0.69 | 2.61 | 0.13 | 3.05 | 0.05 |
| | 5 min | 2.69 | 0.39 | 3.58 | 0.57 | 3.42 | 0.58 |
| | 10 min | 2.98 | 0.04 | 3.74 | 0.28 | 4.12 | 1.03 |
| Level 3 | 1 min | 2.60 | 0.23 | 3.98 | 0.26 | 2.72 | 0.42 |
| | 5 min | 4.26 | 0.11 | 4.88 | 0.24 | 4.54 | 2.91 |
| | 10 min | 4.27 | 0.14 | 6.16 | 2.51 | 4.55 | 0.38 |

The above results show that a log reduction of 4 logs is achieved for the level 3 concentration of *Staphylococcus aureus* on all surfaces tested at both 5 minute and 10 minute contact times. This indicates a clearly effective activity against bacteria. Lower concentration levels (level 2 on the vinyl surface with 10 minutes contact time) and lower contact time (level 3 on ceramic surface with 1 minute contact time) experiments approached this performance. These results show that the formulation reduces the bacterial count of *Staphylococcus aureus* to an effective extent.

*Pseudomonas aeruginosa*, Perlite+Sodium Dichloroisocyanurate

TABLE 3

| Level | Contact time | Wood Mean | Wood s.d | ceramic mean | ceramic s.d | Vinyl Mean | vinyl s.d |
|---|---|---|---|---|---|---|---|
| Level 1 | 1 min | 2.54 | 0.07 | 3.54 | 0.02 | 2.41 | 0.08 |
| | 5 min | 2.60 | 0.07 | 3.80 | 0.86 | 2.67 | 0.02 |
| | 10 min | 2.54 | 0.20 | 3.54 | 0.26 | 2.58 | 0.03 |

TABLE 3-continued

| Level | Contact time | Wood Mean | Wood s.d | ceramic mean | ceramic s.d | Vinyl Mean | vinyl s.d |
|---|---|---|---|---|---|---|---|
| Level 2 | 1 min | 2.59 | 0.10 | 4.39 | 0.15 | 2.47 | 0.16 |
| | 5 min | 3.37 | 0.20 | 4.61 | 1.27 | 2.87 | 0.06 |
| | 10 min | 3.75 | 0.14 | 5.00 | 0.52 | 4.82 | 2.18 |
| Level 3 | 1 min | 5.07 | 1.22 | 5.97 | 0.35 | 4.20 | 1.79 |
| | 5 min | 6.52 | 1.43 | 7.11 | 0.83 | 5.75 | 0.65 |
| | 10 min | 5.98 | 2.20 | 6.20 | 0.14 | 6.81 | 0.08 |

The level 3 concentration provides a 4 log reduction in the activity of *Pseudomonas aeruginosa* on all three surfaces tested and within 1 minute contact time. The level 2 concentration matches this sterilisation performance on ceramic, again for all three tested contact times, and approaches or exceeds this performance for this bacteria for 10 minutes contact time on all surfaces. These results show that the formulation reduces the bacterial count of *Pseudomonas aeruginosa* to an effective extent.

The next two sets of test results relate to fungicidal activity.

*Candida albicans*, Perlite+Dichloroisocyanurate

TABLE 4

| Level | Contact time | wood mean | wood s.d | ceramic mean | ceramic s.d | vinyl mean | vinyl s.d |
|---|---|---|---|---|---|---|---|
| Level 1 | 1 min | 1.50 | 0.28 | 2.56 | 0.17 | 2.16 | 0.07 |
| | 5 min | 1.32 | 0.24 | 1.91 | 0.72 | 1.75 | 0.20 |
| | 10 min | 1.71 | 0.11 | 1.92 | 0.44 | 1.86 | 0.24 |
| Level 2 | 1 min | 1.81 | 0.10 | 2.76 | 0.14 | 3.10 | 0.71 |
| | 5 min | 2.79 | 1.73 | 2.67 | 0.27 | 3.25 | 1.01 |
| | 10 min | 1.91 | 0.71 | 3.09 | 1.50 | 2.46 | 0.01 |
| Level 3 | 1 min | 1.97 | 0.97 | 2.84 | 1.17 | 2.47 | 0.17 |
| | 5 min | 2.08 | 1.17 | 2.43 | 0.03 | 2.14 | 0.15 |
| | 10 min | 1.79 | 0.31 | 2.39 | 0.71 | 3.06 | 0.64 |

*Aspergillus brasiliensis* (Conidiospores), Perlite+Dichloroisocyanurate

TABLE 5

| Level | Contact time | wood mean | wood s.d | ceramic mean | ceramic s.d | vinyl mean | vinyl s.d |
|---|---|---|---|---|---|---|---|
| Level 1 | 1 min | 1.56 | 0.37 | 1.94 | 0.12 | 0.96 | 0.41 |
| | 5 min | 1.18 | 0.21 | 2.21 | 0.18 | 0.74 | 0.15 |
| | 10 min | 1.58 | 0.30 | 2.11 | 0.11 | 0.78 | 0.14 |
| Level 2 | 1 min | 1.48 | 0.49 | 2.12 | 0.28 | 1.06 | 0.34 |
| | 5 min | 1.52 | 0.29 | 2.29 | 0.57 | 1.33 | 0.01 |
| | 10 min | 1.92 | 0.10 | 2.40 | 0.06 | 1.12 | 0.26 |
| Level 3 | 1 min | 2.28 | 0.66 | 2.42 | 0.48 | 0.97 | 0.25 |
| | 5 min | 1.73 | 1.73 | 2.92 | 0.50 | 1.30 | 0.04 |
| | 10 min | 1.69 | 1.69 | 2.76 | 0.63 | 1.13 | 0.50 |

The disinfectant product showed a sterilization activity of >3 log reduction against *C. albicans* (yeast, vegetative cells) on vinyl surfaces at the 10.0% W/W and 20.0% W/W concentrations surfaces at 5 minutes at 20° C. This is an effective result for this yeast. Regarding *A. brasiliensis* (filamentous fungus, conidiospores) the data tabulated in Table 5 here show some activity on the surfaces tested. It should also be noted, that the standard contact time for defining disinfectant action against fungi is 15 minutes, and further experiments indicate favourable behaviour as a yeasticidal disinfectant with contact times of 15 minutes.

Results for endospores are now presented.
*Bacillus subtilis* (Endopores), Perlite+Dichloroisocyanurate

TABLE 6

| Level | Contact time | wood mean | wood s.d | ceramic mean | ceramic s.d | vinyl mean | vinyl s.d |
|---|---|---|---|---|---|---|---|
| Level 1 | 1 min | 2.80 | 0.52 | 3.17 | 0.03 | 2.88 | 0.13 |
|  | 5 min | 2.78 | 0.47 | 3.20 | 0.06 | 2.99 | 0.22 |
|  | 10 min | 2.51 | 0.17 | 3.10 | 0.07 | 2.95 | 0.05 |
| Level 2 | 1 min | 2.74 | 0.09 | 3.19 | 0.09 | 2.85 | 0.07 |
|  | 5 min | 2.95 | 0.45 | 3.14 | 0.23 | 2.88 | 0.14 |
|  | 10 min | 2.69 | 0.14 | 3.08 | 0.11 | 3.09 | 0.21 |
| Level 3 | 1 min | 2.66 | 0.42 | 3.13 | 0.10 | 2.80 | 0.39 |
|  | 5 min | 2.79 | 0.15 | 3.27 | 0.10 | 3.12 | 0.30 |
|  | 10 min | 2.78 | 0.38 | 2.99 | 0.21 | 2.80 | 0.22 |

The above results show sporicidal activity well above a log reduction of 2 logs for *Bacillus subtilis* on all three tested surfaces, at all three concentrations tested, and this from a contact time of 1 minute. This is a highly effective result for activity against spore strains.

The final three sets of results are for viruses. The three test viruses, Adenovirus-5, Poliovirus-1 and Murine parvovirus, are standard naked virus strains with established high chemical resistance to biocides. Efficacy against these standard viruses represents activity against all known human viruses and veterinary viruses. The results for these final three tests are discussed together.

Adenovirus-5, Perlite+Dichloroisocyanurate

TABLE 7

| Level | Contact time | wood mean | wood s.d | ceramic mean | ceramic s.d | vinyl mean | vinyl s.d |
|---|---|---|---|---|---|---|---|
| Level 1 | 1 min | 6.26 | 0.62 | 5.20 | 0.00 | 6.11 | 0.12 |
|  | 5 min | 6.35 | 0.49 | 5.20 | 0.00 | 6.11 | 0.12 |
|  | 10 min | 6.35 | 0.49 | 5.11 | 0.12 | 6.20 | 0.00 |
| Level 2 | 1 min | 6.35 | 0.49 | 5.11 | 0.12 | 5.95 | 0.35 |
|  | 5 min | 6.35 | 0.49 | 5.20 | 0.00 | 6.20 | 0.00 |
|  | 10 min | 6.18 | 0.73 | 5.03 | 0.23 | 6.11 | 0.12 |
| Level 3 | 1 min | 6.10 | 0.85 | 4.70 | 0.00 | 6.20 | 0.00 |
|  | 5 min | 6.18 | 0.49 | 5.20 | 0.00 | 6.20 | 0.00 |
|  | 10 min | 6.26 | 0.37 | 5.03 | 0.23 | 6.20 | 0.00 |

Poliovirus-1, Perlite+Dichloroisocyanurate

TABLE 8

| Level | Contact time | wood mean | wood s.d | ceramic mean | ceramic s.d | vinyl mean | vinyl s.d |
|---|---|---|---|---|---|---|---|
| Level 1 | 1 min | 3.11 | 0.12 | 3.36 | 0.00 | 4.54 | 0.00 |
|  | 5 min | 3.03 | 0.23 | 3.44 | 0.59 | 4.70 | 0.00 |
|  | 10 min | 2.95 | 0.59 | 3.69 | 0.23 | 5.37 | 0.24 |
| Level 2 | 1 min | 2.78 | 0.35 | 2.94 | 0.83 | 5.20 | 0.00 |
|  | 5 min | 3.62 | 1.06 | 3.36 | 0.47 | 5.87 | 0.00 |
|  | 10 min | 4.78 | 0.12 | 2.94 | 0.12 | 5.04 | 0.71 |
| Level 3 | 1 min | 3.70 | 0.24 | 3.28 | 1.06 | 4.95 | 1.06 |
|  | 5 min | 4.20 | 1.41 | 5.03 | 0.00 | 4.95 | 0.83 |
|  | 10 min | 4.53 | 0.71 | 4.03 | 1.17 | 5.03 | 0.47 |

Murine Parvovirus, Perlite+Dichloroisocyanurate

TABLE 9

| Level | Contact time | wood mean | wood s.d | ceramic mean | Ceramic s.d | vinyl mean | vinyl s.d |
|---|---|---|---|---|---|---|---|
| Level 1 | 1 min | 2.44 | 0.12 | 2.78 | 0.12 | 2.45 | 0.12 |
|  | 5 min | 2.53 | 0.24 | 2.95 | 0.12 | 2.62 | 0.11 |
|  | 10 min | 3.03 | 0.00 | 3.20 | 0.23 | 2.62 | 0.11 |
| Level 2 | 1 min | 3.44 | 0.12 | 3.87 | 0.00 | 3.70 | 0.23 |
|  | 5 min | 3.53 | 0.47 | 4.53 | 0.23 | 4.70 | 0.00 |
|  | 10 min | 5.03 | 0.00 | 4.78 | 0.12 | 4.87 | 0.00 |
| Level 3 | 1 min | 4.03 | 0.00 | 3.70 | 0.00 | 3.78 | 0.12 |
|  | 5 min | 5.03 | 0.00 | 4.87 | 0.00 | 4.87 | 0.00 |
|  | 10 min | 5.03 | 0.00 | 4.87 | 0.00 | 4.87 | 0.00 |

Overall, the data show that an antiviral activity corresponding to a reduction of ≥4 log for adenovirus and murine parvovirus, and an antiviral activity corresponding to a reduction of ≥3 log for poliovirus, was achieved between 1 minute and 5 minutes contact for the 20.0% W/W Perlite+dichloroisocyanurate based product. This corresponds to a high level of virucidal activity for each of these individual organisms.

Against adenovirus-5 the disinfectant product showed very high level virucidal activity (>6 log reduction) at 1.0%, 10.0% and 20.0% W/W dichloroisocyanurate (levels 1, 2 and 3) within one minute on wood and vinyl surfaces. The same formulation at all three tested concentrations also showed very effective action (>5 log reduction) against adenovirus-5 within one minute on ceramic surfaces.

Poliovirus −1 is a high chemical resistance virus with a log reduction acceptance criterium of ≥3 logs. On vinyl surfaces, this virus showed a >4.0 log reduction at 1.0%, in one minute and a 5.00 log reduction (ranging from 4.95 to 5.87) after 1 minute at 10.0% and 20.0% W/W. On wood surfaces, the activity was lower, but still virucidal, achieving >4.0 log reductions in 10 minutes at 10.0% W/W and within 5 minutes at 20.0% W/W. On ceramic surfaces, a >4.0 log reduction was achieved after 10 minutes at 20.0% W/W.

The 10% W/W, Level 2, formulation showed activity of respective log reductions on all three surfaces, wood, ceramic and vinyl, within 5 minutes, and complete kill after 10 minutes. The level 3 formulation achieved the same rate of complete kill on all surfaces within 5 minutes. Thus, this formulation was completely effective at 10.0% W/W within 10 minutes and at 20.0% W/W in 5 minutes against murine parvovirus on the surfaces tested. The efficacy at 1 minute was in the range 3-4 log reductions for both the 10.0% and 20.0% W/W formulations.

The invention claimed is:

1. A dry biocidal absorbent composition comprising an interspersed mixture of dry expanded perlite and a dry biocide.

2. A composition as claimed in claim 1, wherein the biocide is an oxidising biocide.

3. A composition as claimed in claim 1, wherein the biocide is a halogenated biocide.

4. A composition as claimed in claim 3, wherein the halogenated biocide comprises an alkali metal halocyanurate.

5. A composition as claimed in claim 4 wherein the alkali metal halocyanurate comprises sodium dichloroisocyanurate or a hydrate thereof.

6. A composition as claimed in claim 1, wherein the biocide comprises bromochlorodimethylhydantoin.

7. A composition as claimed in claim 1, wherein the biocide comprises a mixture of sodium percarbonate and tetraacetylethylenediamine.

8. A method of using a dry biocidal absorbent composition comprising the following steps:

applying a quantity of a composition comprising an interspersed mixture of dry expanded perlite and a dry biocide;

leaving the formulation in place for a period of time to form a residue; and removing the residue for disposal.

9. A container containing a quantity of the composition according to claim 1.

10. A method of preparing a composition, comprising mixing a dry biocide with dry expanded perlite.

11. The method of claim 8, wherein the applying step comprises applying the quantity of the composition onto a bodily spill on a floor or other surface.

12. The method of claim 8, wherein the applying step comprises applying the quantity of the composition on surfaces of a bin to sanitize the bin.

13. The method of claim 8, wherein the applying step comprises applying the quantity of the composition onto surfaces in areas where livestock are or have been kept or confined as a cleaning composition or disinfectant.

14. The method of claim 8, wherein the applying step comprises applying the quantity of the composition onto land or ground as a sanitizer.

15. The method of claim 10, wherein the biocide comprises a halogenated biocide.

16. The method of claim 15, wherein the halogenated biocide comprises an alkali metal halocyanurate.

17. The method of claim 16, wherein the alkali metal halocyanurate comprises sodium dichloroisocyanurate or a hydrate thereof.

* * * * *